United States Patent [19]

Miyatake et al.

[11] Patent Number: 4,593,197
[45] Date of Patent: Jun. 3, 1986

[54] GAS ANALYZER

[75] Inventors: Kimio Miyatake; Junji Aoki, both of Kyoto, Japan

[73] Assignee: Horiba, Ltd., Kyoto, Japan

[21] Appl. No.: 699,394

[22] Filed: Feb. 7, 1985

[30] Foreign Application Priority Data

Apr. 7, 1984 [JP] Japan ............... 59-51621[U]

[51] Int. Cl.[4] .............................................. G01J 1/00
[52] U.S. Cl. ..................................... 250/343; 250/338
[58] Field of Search ............ 250/338 R, 338 PY, 343, 250/345; 356/437, 440, 442

[56] References Cited

U.S. PATENT DOCUMENTS

| | | | |
|---|---|---|---|
| 2,750,834 | 6/1956 | Golay | 250/343 |
| 4,008,394 | 2/1977 | Risgin et al. | 250/343 |
| 4,072,424 | 2/1978 | McMullan et al. | 356/442 |
| 4,204,768 | 5/1980 | N'Guyen | 250/343 |

*Primary Examiner*—Janice A. Howell

*Attorney, Agent, or Firm*—Wenderoth, Lind & Ponack

[57] ABSTRACT

A gas analyzer has a generally cylindrical cell having cell windows closing the opposite ends thereof and which are infrared passing materials and pipes for passing a sample gas through the cell, a source of infrared radiation at one end of the cell, a chopper at the other end of the cell, and a sensing part of the other end of the cell on the opposite side of the chopper from the cell. The sensing part has a plurality of dual pyroelectric sensors spaced around the axis of the cell and each having a pair of elements constituted by a light receiving element for receiving infrared radiation which has passed through the cell and an auxiliary element, the pair of elements in each sensor being positioned substantially radially relative to the axis of the cell with the light receiving element radially inwardly of the auxiliary element and lying within the cross-section of the inner peripheral surface of the cylindrical cell and the auxiliary element lying outside the cross-section.

1 Claim, 6 Drawing Figures

GAS ANALYZER

BACKGROUND OF THE INVENTION

1. Field of the Invention

The present invention relates to an improvement in a gas analyzer for measuring concentration of specific constituents in the sample gas, particularly to an improvement in a gas analyzer using dual type pyroelectric sensors.

2. Description of the Prior Art

FIG. 1 shows an example of a dual type pyroelectric sensor DP (hereinafter called simply a dual pyroelectric sensor) comprising two pairs of electrodes $2a$ and $2b$ and $3a$ and $3b$ provided on the front and reverse sides of a single piece of pyroelectrical material 1, all of the abovesaid components being contained in a package 4, the package having an opening covered by a filter 5 serving as a light receiving element in line with one pair of electrodes $2a$ and $2b$, and a further opening covered a radiation blocking plate 6 serving as an auxiliary element in line with the other pair of electrodes $3a$ and $3b$. The dual type pyroelectric sensor having the structure as described has excellent noise characteristics due to temperature changes or vibration as compared with the so-called single type pyroelectric sensor containing no more than one pair of electrodes in a package. Therefore, it is currently favored for use in the sensing part of the gas analyzer.

FIG. 2 and FIG. 3 show an example of a conventional gas analyzer using dual pyroelectric sensors DP as described above.

In FIG. 2, the reference numeral 11 designates a light source emitting infrared rays and reference numeral 12 designates a cell through which infrared rays are projected from the light source 11. The cell is closed at both ends thereof by cell windows 13 and 14 composed of an infrared ray passing material, and is provided with an inlet port 15 and outlet port 16 for introducing and discharging the sample gas.

The reference numeral 17 designates a sensing part for sensing constituents (for example, CO, $CO_2$, HC, etc.) of the above-said sample gas to be analyzed, and which is disposed to receive infrared rays passing through the cell 12. The numeral 18 designates a chopper between the cell and the sensing part and having a shaft 18' extending to a driving motor (not shown). As shown in FIG. 3, in the sensing part 17, are four dual pyroelectric sensors $DP_1$, $DP_2$, $DP_3$, and $DP_4$, the first three being for sensing CO, $CO_2$ and HC, respectively, and the fourth one for reference. The filters 5 of the dual pyroelectric sensors $DP_1$ through $DP_4$ are bandpass filters which permit passage of infrared rays of a specific absorption band corresponding to the material to be measured therethrough. For example, the filter 5 of the dual pyroelectric sensor $DP_1$ for sensing CO is a band-pass filter permitting infrared rays of an absorption band specific to CO to pass therethrough. The filters of the dual sensors $DP_2$ and $DP_3$ pass infrared rays specific to $CO_2$ and HC. On the other hand, the filter of the reference dual pyroelectric sensor $DP_4$ is a bandpass filter which permits infrared rays of wavelengths lying outside the absorption bands specific to CO, $CO_2$, and HC to pass therethrough.

In the conventional gas analyzer, as shown in FIG. 3, dual pyroelectric sensors $DP_1$ through $DP_4$ are in an arrangement for enabling all light receiving elements and auxiliary elements, as a whole, to be completely encircled by the inner periphery 12' of the cell 12, so that the diameter of the cell is naturally quite large. Accordingly, the internal volume of the cell 12 is large and requires a large volume of the sample gas to fill it, whereby the length of time this gas stays in the cell 12 is prolonged, a period of response time before the appearance of a stable output is also increased, and this in turn causes problems in the response characteristic, the density energy acting upon each light receiving element 2 is low, and the S/N ratio is unsatisfactory.

One conceivable way of coping with the above described problem is to reduce the distance between each pair of dual pyroelectric sensors $DP_1$ through $DP_4$ and also to reduce the inner diameter d of the cell. However it is impossible to arrange the dual pyroelectric sensors $DP_1$ through $DP_4$ any closer to each than a certain distance because the revolving shaft 18' of the chopper 18 passes through a space encircled by the dual pyroelectric sensors $DP_1$ through $DP_4$ so as to be connected to a driving motor (not shown).

Another way is to shorten the length l of the cell 12. However, at some times low concentrations of CO and HC cannot be measured because the length l of the cell is too short.

SUMMARY OF THE INVENTION

The inventor of the present invention made the present invention with the above problems in mind. Therefore, an object of the present invention is to reduce the inner diameter of the cell of a gas analyzer provided with two or more dual pyroelectric sensor units for facilitating miniaturization of this kind of gas analyzer while increasing the response speed as well as raising the S/N ratio.

A gas analyzer according to the present invention provided with two or more pyroelectric sensor units has the light receiving element of each pyroelectric sensor disposed in a position lying on the side of the unit nearest the center of the small diameter cell.

In a gas analyzer having such a structure, since the inner diameter is reduced and, therefore, the internal volume of the cell is reduced to about 60 to 70% of that of a conventional cell, the length of time the sample gas stays in the cell can be markedly reduced. Accordingly, the response time is further shortened and the density of energy acting upon each light receiving element is increased, thereby raising the S/N ratio. Moreover, the reduced dimeter of the cell contributes to miniaturization of the gas analyzer and makes it possible to reduce the price thereof.

DESCRIPTION OF THE PREFERRED EMBODIMENT

Figure 2:
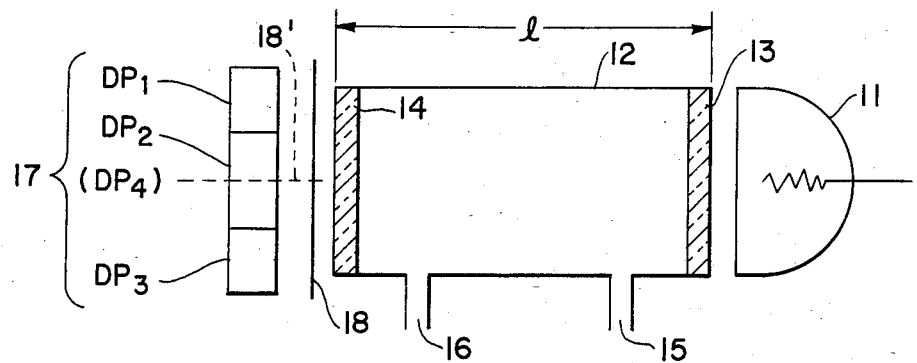
FIG. 2 is a schematic sectional view of the structure of a conventional gas analyzer.
Figure 3:
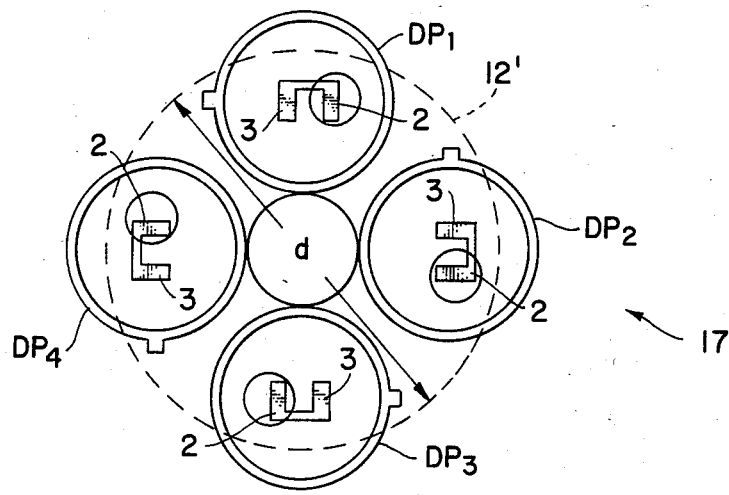
FIG. 3 is a front elevation view of the sensing part thereof.
Figure 4:
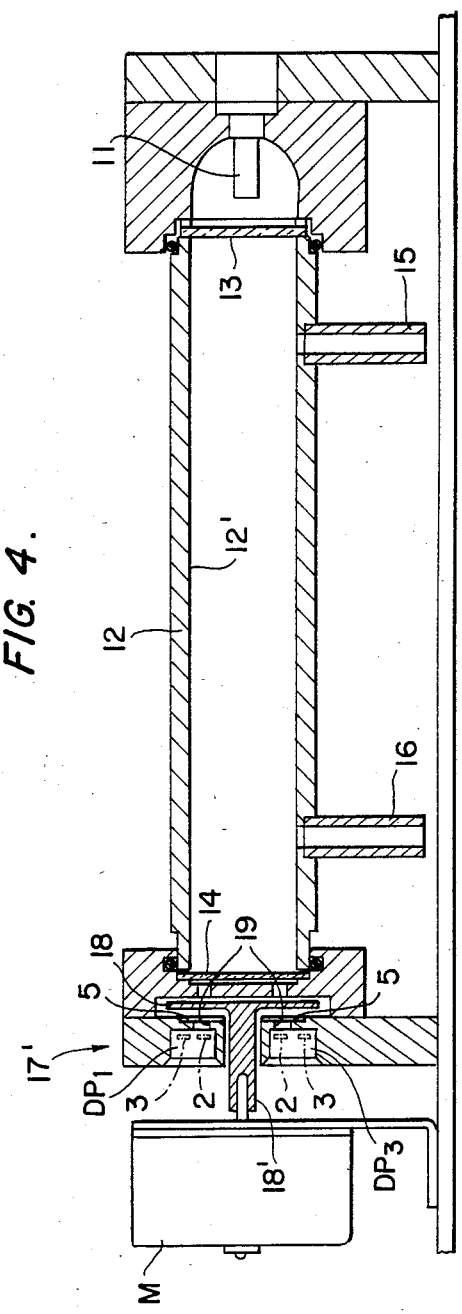
FIG. 4 is a vertical side sectional view of a gas analyzer according to this invention.

In FIG. 4 the same reference numerals and characters as those used in FIG. 2 are applied to the same or corresponding parts. The gas analyzer has a light source 11 emitting infrared rays and a generally cylindrical cell 12 through which the infrared rays are projected from the light source 11. The cell is closed at both ends by cell windows 13 and 14 composed of infrared passing material, and is provided with an inlet port 15 and an outlet port 16 for introducing and discharging sample gas.

The sensing part of the present invention is designated 17' and includes the same elements as the sensing part of the prior art gas analyzer, but in a different arrangement, and the chopper 18 between the cell and the sensing part with the shaft 18' extending to the motor M. The sensing part has the four dual pyroelectric sensors $DP_1$, $DP_2$, $DP_3$ and $DP_4$ each having the light receiving element 2, auxiliary element 3, filter 5 and shelter plate 6 with the filters 5 being band pass filters for passing the infrared rays of a specific absorption band corresponding to the material to be measured therethrough.

Figure 5:
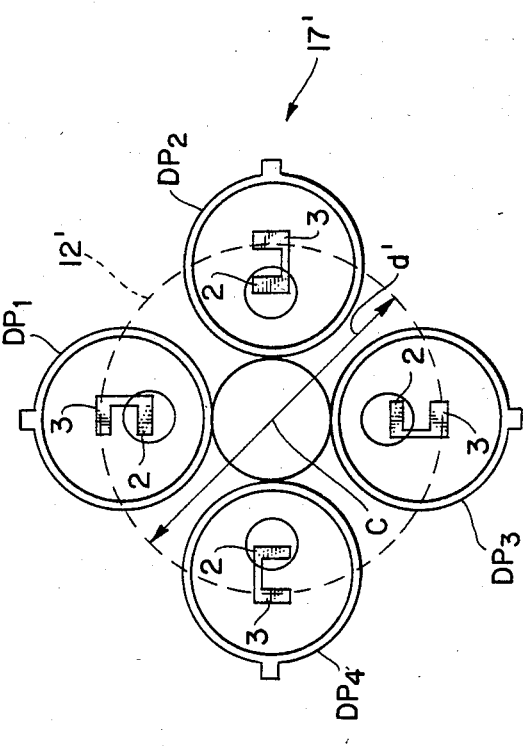
FIG. 5 is a front elevation view of the sensing part thereof.

As seen from FIG. 5, each of the light receiving elements 2 of the four dual pyroelectric sensor units $DP_1$ through $DP_4$ composing the sensing part 17' is at a position radially inwardly toward the center axis C of the cell 12 from the other element 3 thereof. The diameter d' of the cell 12 is such that in each of the dual pyrosensors $DP_1$ through $DP_4$, only the light receiving element 2 lies within the cross-section of the inner peripheral surface 12' of the cell 12, while the auxiliary element 3 not receiving rays of light lies outside, in the radial direction, of the periphery of the cell 12.

Figure 1:
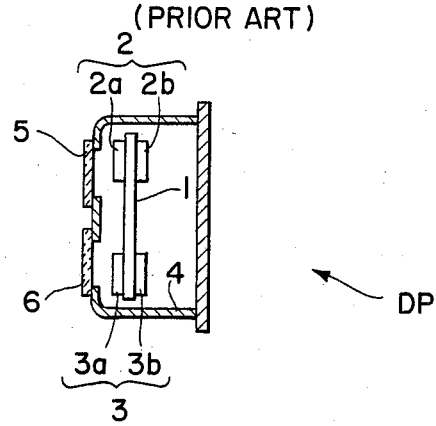
FIG. 1 is a schematic sectional view of a conventional dual type pyroelectric sensor in general use.
Figure 6:
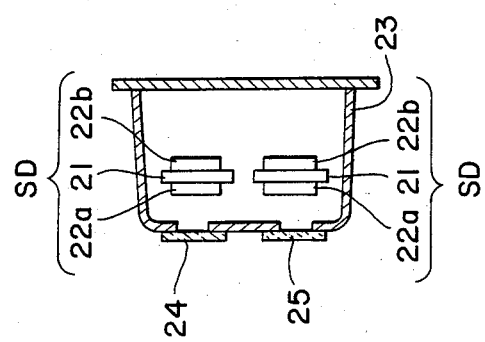
FIG. 6 is a sectional view showing an example of the structure of another dual type pyroelectric sensor which can be used in this invention.

Each of the dual pyroelectric sensor units $DP_1$ through $DP_4$ of this embodiment comprises two pairs of electrodes 2a and 2b and 3a and 3b positioned on both sides of a single piece of pyroelectrical material 1 so that these components are all contained in one package 4 (structurally the same as that shown in FIG. 1). The sensor units may, however, comprise, as shown in FIG. 6 a pair of single type pyroelectric sensors SD on both sides of respective pieces of pyroelectrical material 21, all of the sensors being contained in one package 23. The sensors SD have electrodes 22a and 22b the same as the electrodes 2a and 2b of the sensors DP, and the filter 24 and shelter plate 25 the same as the filter 5 and shelter 6 of the sensors DP. Pyroelectric sensors of this type are also dual pyroelectric sensors within the meaning of that term as used in this patent application.

What is claimed is:

1. A gas analyzer comprising: a generally cylindrical cell having cell windows closing the opposite ends thereof and which are infrared passing material and means for passing a sample gas through said cell, a source of infrared radiation at one end of said cell, a chopper at the other end of said cell, and a sensing part at the other end of said cell on the opposite side of said chopper from said cell, and sensing part having a plurality of dual pyroelectric sensors spaced around the axis of said cell and each having a pair of elements constituted by a light receiving element for receiving infrared radiation which has passed through said cell and an auxiliary element, said pair of elements in each sensor being positioned substantially radially relative to the axis of said cell with the light receiving element radially inwardly of said auxiliary element and lying within the cross-section of the inner peripheral surface of said cylindrical cell and said auxiliary element lying outside said cross-section.

* * * * *